United States Patent
Silvestre Duarte et al.

(10) Patent No.: US 12,268,206 B2
(45) Date of Patent: Apr. 8, 2025

(54) DIFFERENTIAL AIR FLOW SYSTEM FOR PROMOTING BOTTOM-UP FREEZING OF BLOOD PLASMA IN COMPRESSED BAGS

(71) Applicant: SMARTFREEZ LDA, Porto Salvo (PT)

(72) Inventors: Andreia Filipa Silvestre Duarte, Sacavém (PT); Pedro Gil Sena Rego, Lisbon (PT); Carlos Duarte Da Silva Completo, Antouguia da Baleia (PT)

(73) Assignee: SMARTFREEZ LDA, Porto Salvo (PT)

( * ) Notice: Subject to any disclaimer, the term of this patent is extended or adjusted under 35 U.S.C. 154(b) by 143 days.

(21) Appl. No.: 17/997,573

(22) PCT Filed: Apr. 28, 2021

(86) PCT No.: PCT/IB2021/053523
§ 371 (c)(1),
(2) Date: Oct. 31, 2022

(87) PCT Pub. No.: WO2021/220186
PCT Pub. Date: Nov. 4, 2021

(65) Prior Publication Data
US 2023/0217917 A1    Jul. 13, 2023

(30) Foreign Application Priority Data
Apr. 30, 2020  (PT) ......................................... 116327

(51) Int. Cl.
*A01N 1/02*    (2006.01)
(52) U.S. Cl.
CPC ... *A01N 1/0252* (2013.01); *A61M 2205/3606* (2013.01); *A61M 2206/10* (2013.01)

(58) Field of Classification Search
CPC .............. A01N 1/0252; A01N 1/0284; A61M 2205/3606; A61M 2205/362;
(Continued)

(56) References Cited

U.S. PATENT DOCUMENTS

| | | | | |
|---|---|---|---|---|
| 4,565,073 A | * | 1/1986 | Lavender | ................. A01N 1/02 220/532 |
| 7,810,340 B2 | * | 10/2010 | Owada | ................. A23L 3/3418 62/410 |

(Continued)

FOREIGN PATENT DOCUMENTS

| CN | 204063738 U | * | 12/2014 |
|---|---|---|---|
| CN | 105202847 A | | 12/2015 |

(Continued)

OTHER PUBLICATIONS

Making a Clear Ice Block from the Bottom up (Year: 2014).*
(Continued)

*Primary Examiner* — Emmanuel E Duke
(74) *Attorney, Agent, or Firm* — Leason Ellis LLP (57) ABSTRACT

This disclosure relates to a method and system for fast freezing of a biological product (such as blood plasma) contained in an individual bag or a plurality of bags. This disclosure relates to a method and a-system for freezing plasma in an individual bag or a plurality of bags, favoring bottom-up ice-growth, by implementing a differential air flow on top and bottom surfaces of a horizontally placed bag or bags filled with plasma. This disclosure relates to a method and a differential air flow system for freezing plasma, wherein the heat transfer coefficient on a bottom of a bag is at least 10 times larger than at a top. This disclosure relates to a differential air flow system and method for (Continued)

freezing plasma, wherein the differential air flow on top and bottom surfaces of a plasma bag is imposed by at least one fan or blower.

18 Claims, 9 Drawing Sheets

(58) Field of Classification Search
CPC ............ A61M 2206/10; A61M 1/0286; A61M 1/0272; A61M 2202/0415; F25D 17/06
See application file for complete search history.

(56) References Cited

U.S. PATENT DOCUMENTS

| | | | | |
|---|---|---|---|---|
| 2004/0012003 | A1* | 1/2004 | Tabushi | C08K 9/02 252/601 |
| 2005/0011202 | A1* | 1/2005 | Voute | F25D 31/001 62/62 |
| 2007/0240432 | A1* | 10/2007 | Voute | A61J 1/165 62/66 |
| 2011/0247349 | A1* | 10/2011 | Cutting | A01N 1/02 62/62 |
| 2018/0177180 | A1* | 6/2018 | Chapman | A61M 1/025 |
| 2020/0107993 | A1* | 4/2020 | Cutting | A01N 1/0263 |

FOREIGN PATENT DOCUMENTS

| | | | | |
|---|---|---|---|---|
| CN | 107347875 | A | | 11/2017 |
| CN | 110220356 | A * | 9/2019 | |
| JP | 2015209995 | A * | 11/2015 | |
| KR | 20100119536 | A * | 11/2010 | ........... A01N 1/0252 |
| RU | 2269078 | C1 * | 1/2006 | |
| RU | 2652994 | C1 * | 5/2018 | |
| WO | WO-2019002399 | A1 * | 1/2019 | ........... A01N 1/0221 |

OTHER PUBLICATIONS

A.-M. Swärd-Nilsson et al., "Factors influencing factor VIII activity in frozen plasma", Vox Sanguinis, vol. 90, No. 1, Feb. 2006, pp. 33-39.

J. Hardwick, "Blood processing", ISBT Science Series, vol. 3, May 9, 2008, pp. 148-176.

International Search Report and Written Opinion for corresponding PCT Application No. PCT/IB2021/053523 dated Aug. 25, 2021 (5 pages).

* cited by examiner

| Experiment | Volume of Plasma (mL) | Freezing time (min) | Factor VIII (%; UI/dL) | | Recovery of Factor VIII (%) |
|---|---|---|---|---|---|
| | | | Initial | After freezing | |
| #1 | 215 | 55 | 81.8 | 81.1 | 99.1 |
| #2 | 247 | 50 | 80.4 | 84.7 | 105.3 |

DIFFERENTIAL AIR FLOW SYSTEM FOR PROMOTING BOTTOM-UP FREEZING OF BLOOD PLASMA IN COMPRESSED BAGS

CROSS-REFERENCE TO RELATED APPLICATIONS

This application is a U.S. National Phase Application under 35 U.S.C. § 371 of International Application No. PCT/IB2021/053523, filed Apr. 28, 2021, which claims priority to Portugal Patent Application No. 116327, filed Apr. 30, 2020, the contents of which are hereby incorporated by reference in their respective entireties.

TECHNICAL FIELD

The present disclosure relates to a method and system for fast freezing of an individual bag or a plurality of individual bags containing a biological product, in particular blood plasma. In particular the present disclosure relates to a differential air flow system for promoting bottom-up freezing of blood plasma in compressed bags.

BACKGROUND

Biological liquids, such as blood plasma, are normally collected from the donor, processed and stored, typically frozen to minimize degradation, until its use. Commonly, bags are the containers of choice for biological liquids, and are made from biocompatible materials. Bags can have several configurations, volume options, safety features and other characteristics to improve the whole process.

Concerning the blood plasma preservation, freezing is a critical step since Fresh Frozen Plasma is the major source of coagulation factors (in particular Factor VIII) used in patient with hemorrhagic disorders. The existing medical and scientific literatures recommended that plasma should be frozen at −25° C. or lower to achieve the highest yield of Factor VIII, and that a reduction in Factor VIII content occurs during freezing when the solidification of plasma takes more than one hour. Therefore, in the last years, several freezers, in particular, those applied to plasma freezing, have been developed for the purpose of rapidly freezing blood plasma contained in bags.

Most of the recent methods and equipment, commonly known as contact/shock freezers, use cooling plates (chilled by a circulating coolant) to fast freeze the plasma bags. Some of them, comprise parallel cooling plates that compress the bags between them promoting fast freezing and homogeneity between bags. Some of this equipment arranged the cooling plates in a vertical plane, while other preferred the horizontal arrangement. However, these geometries can result in the loss of the product, or in the reduced activity of Factor VIII. During freezing, pure ice is formed and the plasma solutes are concentrated in the remaining water and each solute form crystals when the solubility of the solutes is exceeded. Using the existing equipment, heat transfer to the bags is highly promoted in both walls of the bag by the compressing cooling plates, thus promoting the ice growth from the walls to the middle of the container, resulting in a heterogeneity in solutes distribution. The solutes will be increasingly concentrated in the middle of the plasma bag, and the molecules of Factor VIII will be exposed to a high concentration of salts for a prolonged period of time, resulting in their inactivation and thus loss of Factor VIII. Moreover, the contact of the plasma bags directly with the cooling plates, may lead to the deformation and rupture of the bag, and consequently loss of the product. To avoid this problem, several frames and boxes have been described, however some of these solutions, in particular the ones made of low conductive materials (plastics), will reduce the heat transfer to the bag, and consequently increasing the freezing time.

Although there are already systems and methods that help to improve the process of plasma freezing, these systems still do not solve the problem of loss of Factor VIII due to freezing heterogeneity (solutes distribution). The uncontrolled freezing geometry is one cause for the heterogeneity in solutes distribution that occurs in frozen solutions of biologics, because it displaces the solutes towards the bottom and center of containers. This is described for various systems, wherein the local composition of the solutes in the ice matrix (per cm3) shows more than 100% variation comparing concentrated regions (typically bottom or center of the containers) with diluted regions (typically on top of containers). Therefore, it is desirable to design a simple and reproducible freezing system of plasma bags, which can be used to freeze multiple bags, while avoiding the solutes heterogeneity. Previous studies show that the heterogeneity in solutes distribution during the freezing process can be reduced by using a controlled freezing geometry, i.e., by freezing from bottom to top (in doi: 10.1002/btpr.1771).

The present disclosure aims at solving the above-mentioned problems, by using a differential air flow system for promoting the bottom-up ice-growth during freezing of blood plasma bags. Another aspect of the present disclosure refers to a case for the plasma bags in order to maintain its integrity and protect them from external stresses, while maintaining the heat transfer at the bottom surface of the bag.

General Description

The present disclosure provides a method and system for freezing plasma bags by using a differential air flow system for promoting the bottom-up ice-growth.

The present disclosure provides a method and system for freezing an individual bag or a plurality of individual bags, favoring bottom-up ice-growth, by implementing a differential air on the upper and bottom surface of a bag horizontally placed.

In the present disclosure, differential air flow means that the heat transfer coefficient on the bottom of the bag is different from the heat transfer coefficient on the top of the bag, preferentially the heat transfer coefficient on the bottom of the bag is 10 times larger than in the top, to favor a bottom-up freezing geometry.

In an embodiment, the differential air flow on the upper and bottom surface of a plasma bag is imposed by at least one fan. A fan or a blower can be used, preferentially a fan is used.

In an embodiment, the differential air flow system may comprise a plurality of fans, preferably one fan per bag.

In an embodiment, the fan should be suitable for use in a cryogenic environment.

In an embodiment, the velocity of the fan may be controlled to conveniently increase or decrease the heat transfer accordingly to the freezing process.

In an embodiment, the velocity of the fan is controlled so that the heat transfer coefficient on the bottom of the bag is 10 times larger than in the top.

In an embodiment, the heat transfer coefficient on the top of the bag must be less than 5 W/(m$^2$.° C.), preferentially less than 2 W/(m$^2$.° C.); and the heat transfer coefficient on the bottom of the bag must be higher than 20 W/(m².° C.), preferentially higher than 50 W/(m².° C.).

In an embodiment, the differential air flow system comprises a flow conveyor to drive the air from the fan to the bottom surface of the plasma bag.

In an embodiment, the air within the flow conveyor has a velocity in a range from approximately 1 m/s to approximately 10 m/s, and more preferably from approximately 2 m/s to approximately 8 m/s.

In an embodiment, the flow conveyor is made of a low heat conductivity, such as plastic, polymer or other material having low conductivity.

In an embodiment, the differential air flow system comprises a support to receive the bag. The support is a grid or a solid metal plate.

In an embodiment, the support may comprise fins to obtain the maximum heat transfer from the air to the support. The fins may have several configurations, assuring the maximum heat transfer from the air to the support.

In an embodiment, the support and the fins may be made of high heat conductive materials such has aluminum, stainless steel, copper, or other.

In an embodiment, the dimensions of the support may vary so it can receive one bag or several. The thickness of the support can be from 1 mm up to 10 mm.

In an embodiment, the fan or a plurality of fans, is perpendicular to the support, directly connected to the flow conveyor.

In an embodiment, the fan or a plurality fans, can be located below the support and the fins.

The present disclosure provides a case to receive a bag, for increasing the freezing consistency, to prevent the nucleation on the top of the bag when compressed and for protection during the freezing and storage of the bag.

In an embodiment, the case may have an opening at the bottom to promote the heat transfer in the bottom surface of the bag.

In an embodiment, the case can be made of polymers, paperboard or other materials that have low heat conductivity. The case can be made of a compressible material. Preferably, the case is made of materials that maintains its integrity even at low temperatures, as for example −50° C.

In an embodiment, the bottom surface of the case may have an opening or a thin film of a high heat conductive material, such as aluminum, to assure the heat transfer to the bottom of the bag inside the case.

In an embodiment, the top surface of the case may have an additional layer of a low heat conductive material in order to prevent the nucleation at the top of the bag.

In an embodiment, the heat transfer coefficient on the top of the case, which is the thermal conductivity of the material divided by its thickness, must be less than 5 W/(m².° C.), preferentially less than 2 W/(m².° C.).

In an embodiment, the case can be designed to receive one bag or a plurality of bags.

In an embodiment, the differential air flow system comprises a compressing means to compress the bag or the case, to increase the contact of the bottom surface against the support.

In an embodiment, the compressing means is made of a rigid material with low heat conductivity, such as plastic, polymer or other material having high rigidity and low conductivity.

In an embodiment, the compressing means may have a furrowed surface in contact with the bag or case, to minimize the heat transfer to the top of the bag. The compressing means may have a rib-or wave-pattern on the surface in contact with the bag or case.

In an embodiment, the compressing means may mechanically actuate to compress the bag or case against the support. The compressing means can also be operated by an automated mechanical actuator.

In an embodiment, the method and system herein disclosed, are designed to be used inside a controlled temperature chamber, for freezing of an individual bag or a plurality of individual bags containing a biological product, in particular blood plasma.

In an embodiment, a temperature probe may be located at one or more points of the differential air flow system or within a case.

In an embodiment, an air velocity probe may be located at one or more points of the differential air flow system, preferentially in the flow conveyor, to provide information about the air flow velocity at a particular location.

An aspect of the present disclosure relates to a method for freezing plasma bags by using a differential air flow system for promoting the bottom-up ice-growth, comprising:
providing a controlled temperature chamber;
placing the differential air flow system into the controlled temperature chamber;
driving the cold air inside the controlled temperature chamber, by the fans and the flow conveyor to the fins and to the support, cooling it;
placing the bag or the case containing the bag horizontally on the support;
compressing the bag or the case against the support by the compressing means;
freezing the bag.

In an embodiment, the method and system of the present invention may be used not only for freezing, but also for thawing.

BRIEF DESCRIPTION OF THE DRAWINGS

These and other objects, features and advantages of the disclosure will be evident from the following detailed description when read in conjunction with the accompanying drawings.

DETAILED DESCRIPTION

In this section, it will be described the fundamentals of the operation of the object of disclosure and of proposed embodiments.

Figure 1:
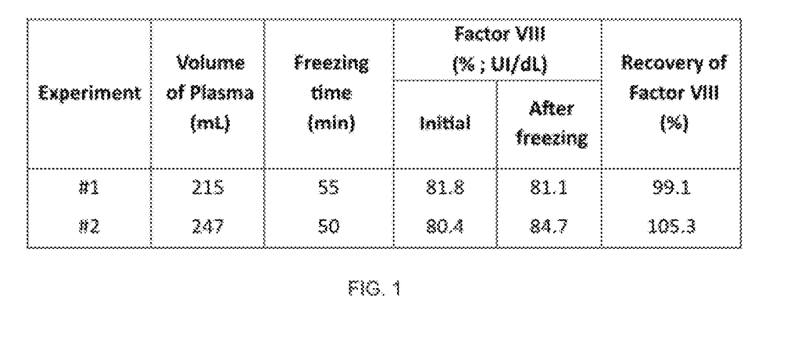
FIG. 1 shows the recovery of the Factor VIII, after freezing two plasma bags inside a controlled temperature chamber at −45° C., by using a differential air flow system for promoting the bottom-up ice-growth, according to the present disclosure.

As described above, one of the major limitations of preservation of biological liquids, such as blood plasma, is the freezing step. During freezing, using the existing methods and equipment, the ice growth from the walls to the middle of the container, and the solutes will be increasingly concentrated in the middle of the plasma bag, and the molecules of Factor VIII will be exposed to a high concentration of salts, resulting in their inactivation and thus loss of Factor VIII. Therefore, we found that by applying a differential air flow (different air flow velocities) on the top and bottom surfaces of a plasma bag (horizontally placed), and by favoring heat transfer from the bottom, a bottom-up freezing geometry was achieved, leading to a high recovery of the Factor VIII (FIG. 1). In this disclosure, differential air flow means that the heat transfer coefficient on the bottom of the bag is different from the heat transfer coefficient on the top of the bag, preferentially the heat transfer coefficient on the bottom of the bag is 10 times larger than in the top, to favor a bottom-up freezing geometry. If we control different heat transfer coefficients, we do not need to control different temperatures, or even add insulation, to achieve the bottom up-freezing geometry. In fact, to attain different heat transfer coefficients, we only need to apply a differential air flow by blowing more air on the bottom of the bag than the top. This method greatly simplifies the system herein disclosed compared to existing systems. Any chamber with controlled temperature can be converted into a high-efficiency, low-maintenance plasma freezer.

Figure 2:
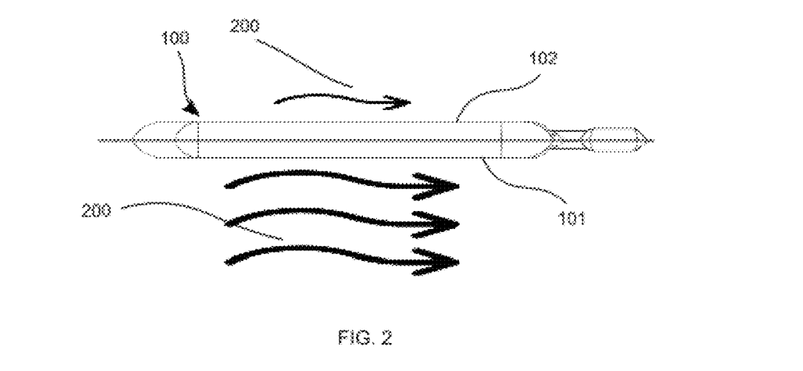
FIG. 2 shows a schematic representation of a differential air flow 200 system for freezing bags 100, favoring bottom-up ice-growth, wherein the heat transfer coefficient on the bottom 101 of the bag is larger than in the top 102.
Figure 3:
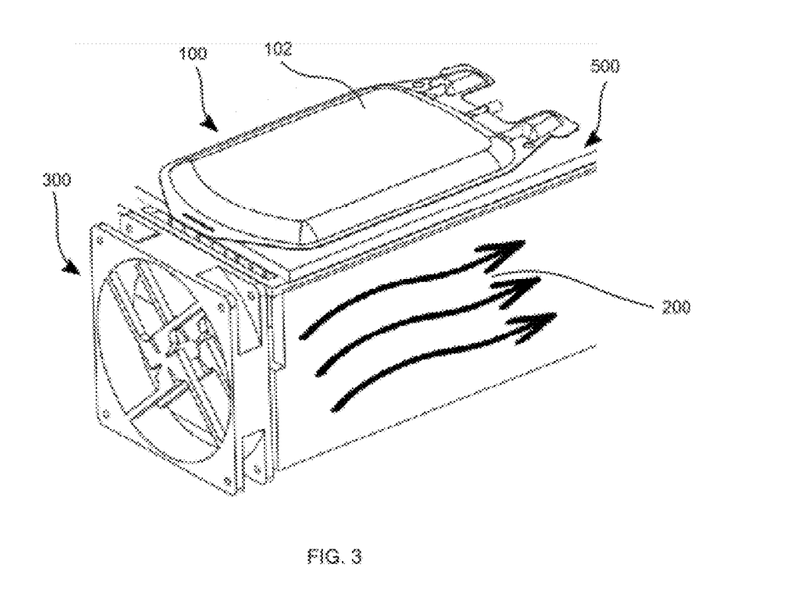
FIG. 3 is schematic and elevated view of a differential air flow system for bags 100 by implementing a differential air flow 200 on the upper 102 and bottom 101 surface of the bag 100 placed in a support 500, by using a fan 300, according to the present disclosure.
Figure 4:
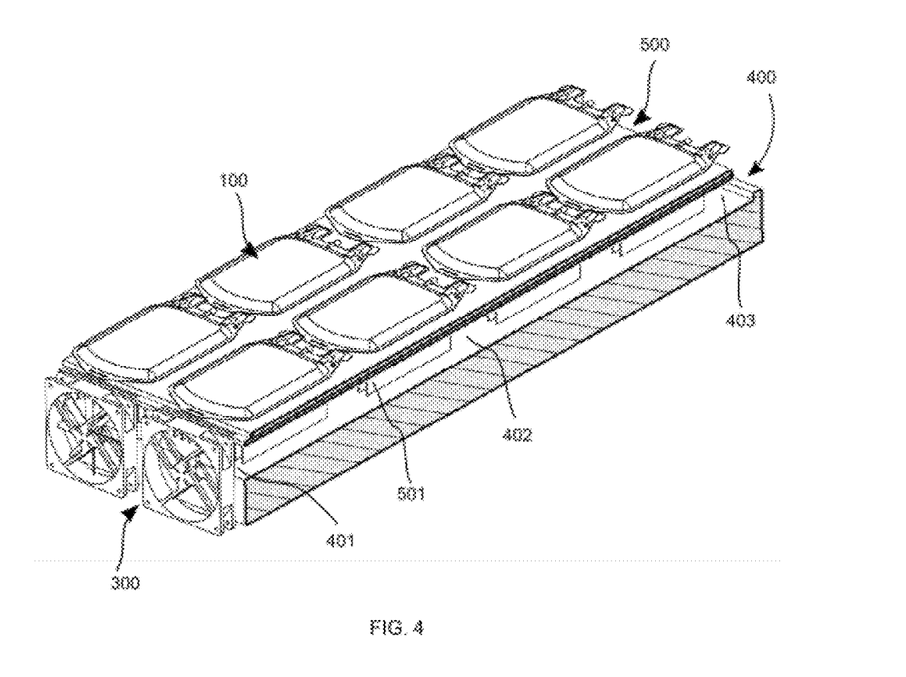
FIG. 4 is an elevated cross-section view of a differential air flow system with a flow conveyor 400, with an entry 401, a channel 402 and an exit 403, to drive the air from the fan 300 through the fins 501 connected to the support 500, to obtain the maximum heat transfer from the air to the support 500, and consequently to the bottom 101 of the bag 100.
Figure 5:
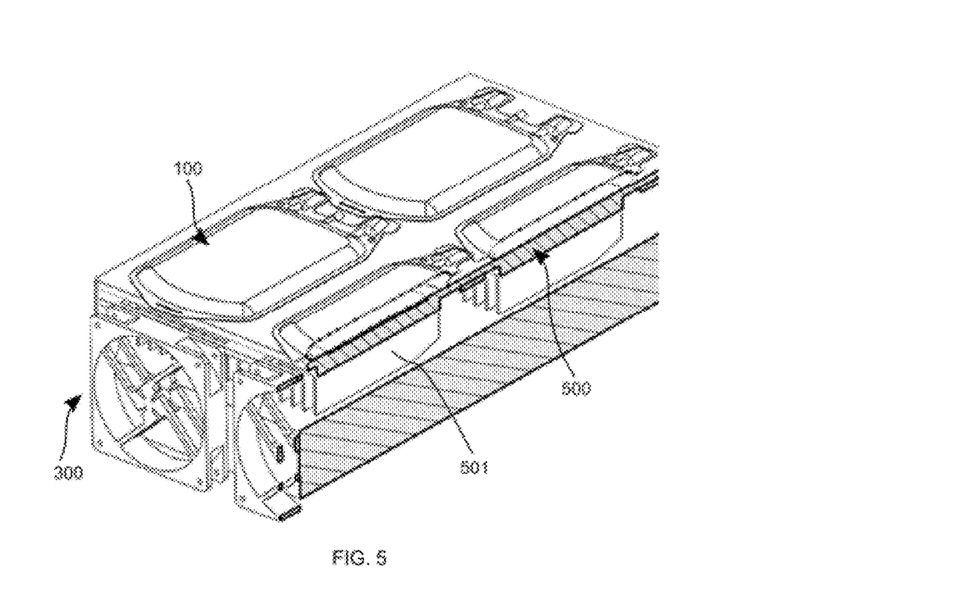
FIG. 5 is an elevated cross-section view of a differential air flow system, showing the support 500 connected to the fins 501 to transfer the heat to the bottom of the bag 100, according to the present disclosure.
Figure 6:
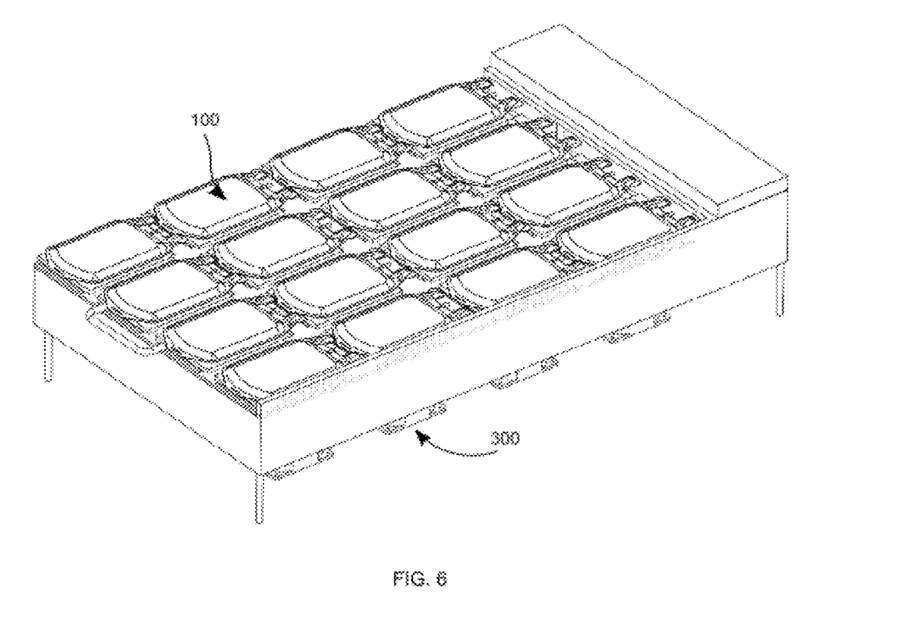
FIG. 6 is an elevated view of a differential air flow system for freezing a plurality of bags 100, comprising a plurality of fans 300, according to the present disclosure.

Therefore, herein, it is disclosed a method and system for freezing an individual bag 100 or a plurality of individual bags, favoring bottom-up ice-growth, by implementing a differential air flow 200 on the upper 102 and bottom 101 surface of a bag horizontally placed. (see FIG. 2 for example illustration)

It is also disclosed a differential air flow system to attain the previously described method, favouring bottom-up ice-growth, by implementing a differential air flow 200 on the upper 102 and bottom 101 surface of a plasma bag 100. In a preferred embodiment, the differential air flow 200 on the upper 102 and bottom 101 surface of a plasma bag 100 is imposed by at least one fan 300. In the embodiment, a fan or a blower can be used, preferentially a fan is used. In another embodiment, the differential air flow system may comprise a plurality of fans, preferably one fan per bag. In a preferred embodiment, said fan should be suitable for use in a cryogenic environment. In another embodiment, the velocity of the fan may be controlled to conveniently increase or decrease the heat transfer accordingly to the freezing process. In a embodiment, the velocity of the fan is controlled so that the heat transfer coefficient on the bottom of the bag is 10 times larger than in the top. In another embodiment, the heat transfer coefficient on the top of the bag must be less than 5 W/(m$^2$.° C.), preferentially less than 2 W/(m$^2$.° C.); and the heat transfer coefficient on the bottom of the bag must be higher than 20 W/(m$^2$.° C.), preferentially higher than 50 W/(m$^2$.° C.). (see FIGS. 2 to 8 for example illustration)

In another embodiment, the differential air flow system comprises a flow conveyor 400 to drive the air from the fan 300 to the bottom 101 surface of the plasma bag. In an embodiment, the flow conveyor 400 may have an entry 401 to the air from the fan 300, a channel 402 through bottom of the bag to drive the air and an exit 403 to the air. In a preferred embodiment, the air within the flow conveyor has a velocity in a range from approximately 1 m/s to approximately 10 m/s, and more preferably from approximately 2 m/s to approximately 8 m/s. In a preferred embodiment, the flow conveyor is made of a low heat conductivity, such as plastic, polymer or other material having low conductivity. (see FIGS. 4 to 8 for example illustration)

In an embodiment, the differential air flow system comprises a support 500 to receive the bag 100. In a preferred embodiment the support 500 is a grid or a solid metal plate. In an embodiment, the support 500 may comprise fins 501 to obtain the maximum heat transfer from the air to the support 500, and consequently to the bottom 101 of the bag. The fins 501 might be attached to the support 500 by means of screws, any type of glue or paste, or by other means, assuring a good thermal conductivity. The fins may have several configurations, assuring the maximum heat transfer from the air to the support. The support and the fins may be made of high heat conductive materials such has aluminum, stainless steel, copper, or other. The dimensions of the support may vary so it can receive one bag or several. The thickness of the support can be from 1 mm up to 10 mm. The support dimensions in a specific configuration are such to have in account the characteristics from the entire system, allowing to have a well-known global thermal conductivity and inertia. (see FIGS. 4 to 8 for example illustration)

In another embodiment, the flow conveyor is designed accordingly to the support and fins to obtain the maximum heat transfer from the air to the bottom of the bag.

In another embodiment, the fan 300 or a plurality of fans, is perpendicular to the support, directly connected to the flow conveyor 400. In another embodiment, the fan 300 or a plurality fans, can be located below the support 500 and the fins 501. In another embodiment, the differential air flow system may comprise a plurality of fans, preferably one fan per bag. (see FIGS. 2 to 8 for example illustration)

Figure 7A:
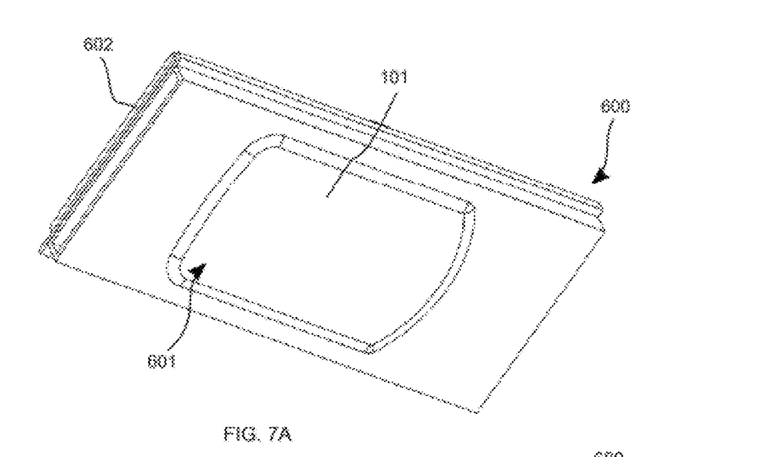
FIG. 7A is a bottom view of a case 600 to receive a bag 100, with an opening 601 at the bottom to promote the heat transfer in the bottom surface 101 of the bag.
Figure 7B:
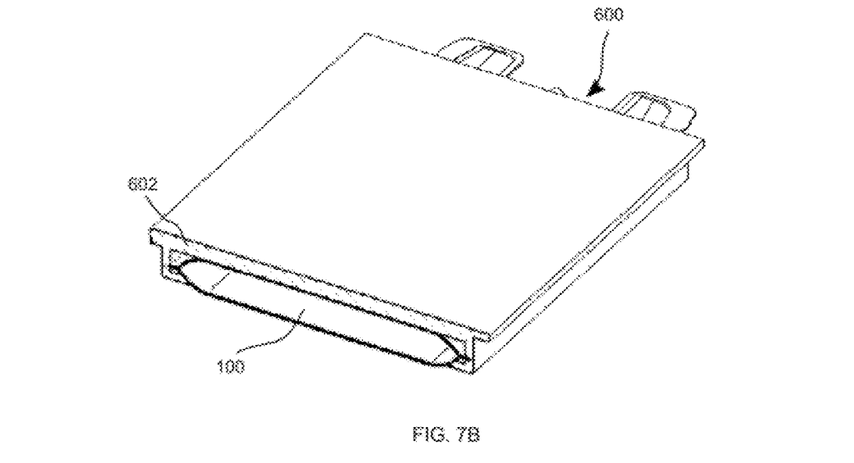
FIG. 7B is an elevated cross-section view of a case 600 to receive a bag 100, with an additional layer 602 of a low heat conductive material in the top of the case.

One exemplary embodiment of the present disclosure is a case 600 to receive a bag 100, for increasing the freezing consistency, to prevent the nucleation on the top of the bag when compressed and for protection during the freezing and storage of the bag. In a preferred embodiment, the case 600 may have an opening 601 at the bottom to promote the heat transfer in the bottom surface 101 of the bag. The case can be made of polymers, paperboard or other materials that have low heat conductivity. In another embodiment, the case can be made of a compressible material, so that when an even-distributed pressure is applied, the case maintains its integrity. Preferably, the case is made of materials that maintains its integrity even at low temperatures, as for example −50° C. In another embodiment, the bottom surface of the case may have an opening or a thin film of a high heat conductive material, such as aluminum, to assure the heat transfer to the bottom of the bag inside the case. In another embodiment, the top surface of the case may have an additional layer 602 of a low heat conductive material in order to prevent the nucleation at the top of the bag. In another embodiment, the case can also have embodiments from any other materials with several functionalities. For example, the case may have an additional opening to assure the reading of information in the bag. The case may have a barcode or a chip to identify the sample. In an embodiment, the case can be designed accordingly to the bag used. In another embodiment, the case can be designed to receive one bag or a plurality of bags. (see FIG. 7 for example illustration)

In an embodiment, the heat transfer coefficient on the top of the case 600, which is the thermal conductivity of the material divided by its thickness 602, must be less than 5 W/(m$^2$.° C.), preferentially less than 2 W/(m$^2$.° C.). In an example, if the case 600 is made of corrugated cardboard (with an average thermal conductivity of 0.064 W/m.° C.), the top of the case 602 must have 1.2 cm of thickness, to obtain a heat transfer coefficient of 5 W/(m$^2$.° C.). In another example, if we use extruded polystyrene (with an average thermal conductivity of 0.025 W/m.° C.) and maintaining the same thickness, we obtain a heat transfer coefficient of W/(m$^2$.° C.).

In another embodiment, the differential air flow system comprises a compressing means 700, to compress the bag 100 or the case 600, to increase the contact of the bottom 101 surface against the support 500. In an embodiment, the compressing means is made of a rigid material with low heat conductivity, such as plastic, polymer or other material having high rigidity and low conductivity. In a preferred embodiment, the compressing means is made of a transparent material. In another embodiment, the compressing means 700 may have a furrowed surface 701 in contact with the bag or case, to minimize the heat transfer to the top of the bag. In a preferred embodiment, the compressing means may have a rib-or wave-pattern on the surface 701 in contact with the bag or case. This pattern will allow a good contact to compress the box, while decreasing the heat transfer to the top of the bag, preventing the nucleation on the top. (see FIG. 8 for example illustration)

Figure 8:
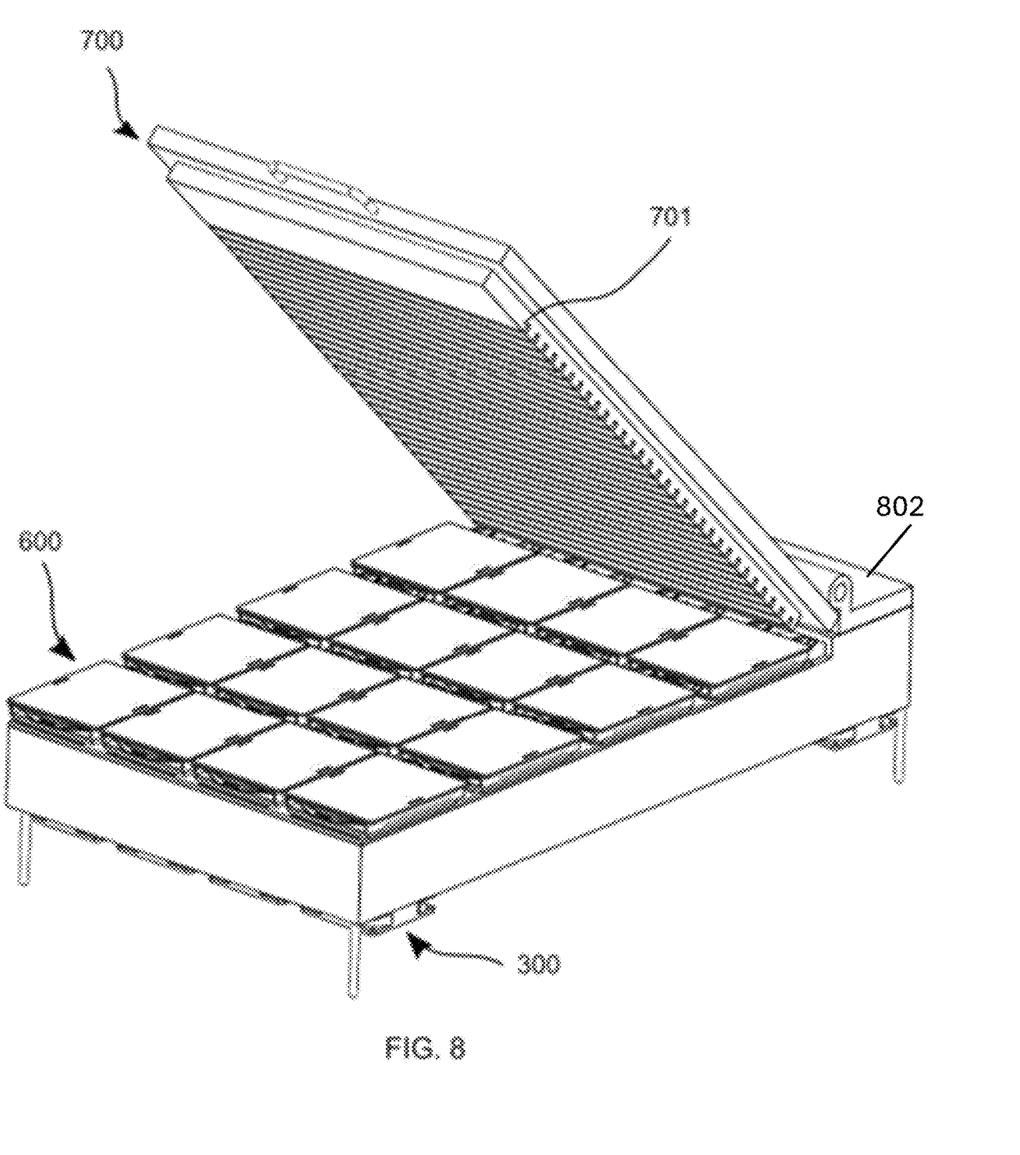
FIG. 8 is an elevated view of a differential air flow system for freezing a plurality of bags 100 inside cases 600, with a compressing means 700 to compress the bags.

In another embodiment, the compressing means may mechanically actuate to compress the bag or case against the support. The compressing means have two positions, open or closed. In an embodiment, the open position is set to load or unload the bags/cases in the differential air flow system and the closed position is set to compress the bags/cases against the support to allow a good heat transfer on the bottom surface of the bag. Moreover, when setting close the compressing mean, all the bags will achieve the same format, allowing a homogenous and reproducible freezing in a plurality of bags. In another embodiment, the compressing means can also be operated by an automated mechanical actuator 802 (FIG. 8).

Figure 14:
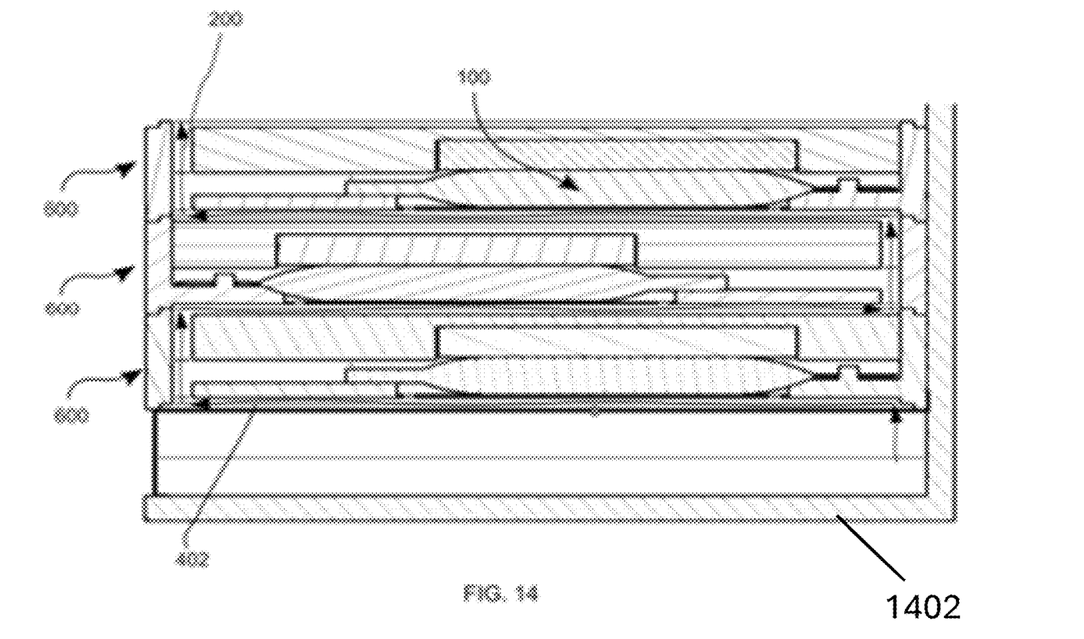
FIG. 14 is a cross-section view of the system in a different configuration. 402 represents the channel for air flow 200.
Figure 15:
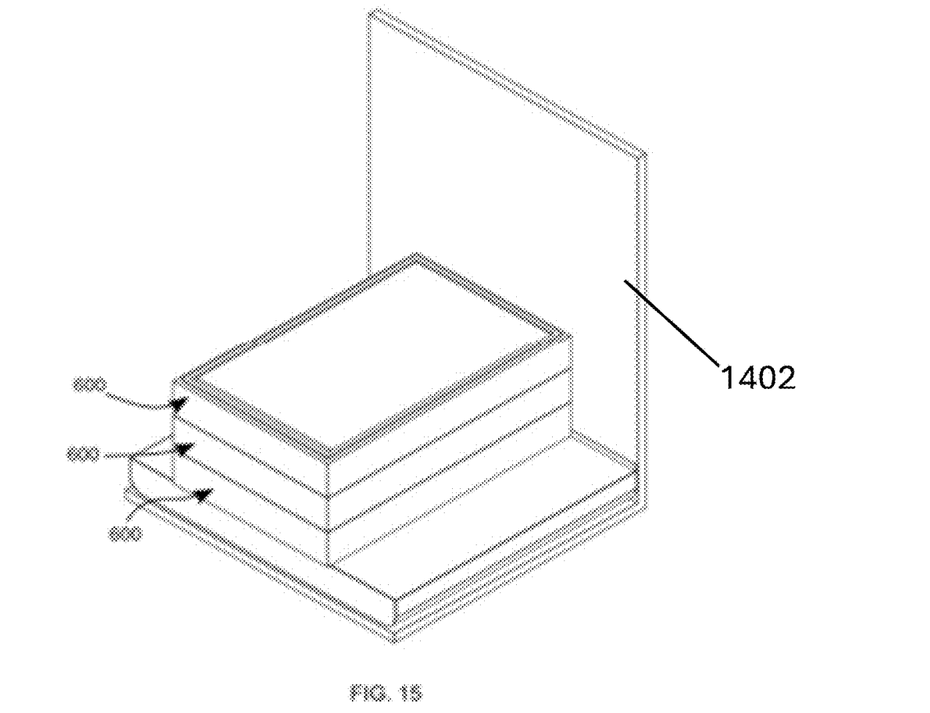
FIG. 15 is an elevated view of the system in a different configuration.

In a preferred embodiment, the method and system herein disclosed, are designed to be used inside a controlled temperature chamber 1402 (FIGS. 14 and 15). The controlled temperature chamber can have or not convection and may be cooled or heated. Briefly, by using the method and differential air flow system herein described, the cold air inside the controlled temperature chamber, will be driven by the fans and the flow conveyor to the fins and to the support, cooling it. When the support is cooled, the case containing the bag is placed on the support, promoting the heat transfer from the support to the bottom of the bag. Finally, the case with the bag is compressed by compressing means, increasing the contact of the bottom bag with the support. This method and differential air flow system will enable the bottom-up ice-growth in a plasma bag, while assuring its homogeneity and integrity.

In a preferred embodiment, the method and system here disclosed allows to use any controlled temperature chamber for freezing of an individual bag or a plurality of individual bags containing a biological product, in particular blood plasma.

In a preferred embodiment, the present disclosure relates to a method for freezing plasma bags by using a differential air flow system for promoting the bottom-up ice-growth, comprising:

providing a controlled temperature chamber;
  placing the differential air flow system into the controlled temperature chamber;
  driving the cold air inside the controlled temperature chamber, by the fans and the flow conveyor to the fins and to the support, cooling it;
  placing the bag or the case containing the bag horizontally on the support;
  compressing the bag or the case against the support by the compressing means;
  freezing the bag.

In an embodiment, a temperature probe may be located at one or more points of the differential air flow system or within a case. The temperature probe may provide an indication of the time-temperature profile during the freezing process. The temperature probe may comprise a thermocouple, a thermistor, or other conventional temperature sensing devices suitable for use in a cryogenic environment.

In another embodiment, an air velocity probe may be located at one or more points of the differential air flow system, preferentially in the flow conveyor, to provide information about the air flow velocity at a particular location. The air velocity probe may comprise an anemometer, pitot tube, or other conventional sensing devices suitable for use in a cryogenic environment.

In an embodiment, the method and differential air flow system of the present invention may be used not only for freezing, but also for thawing.

Figure 9:
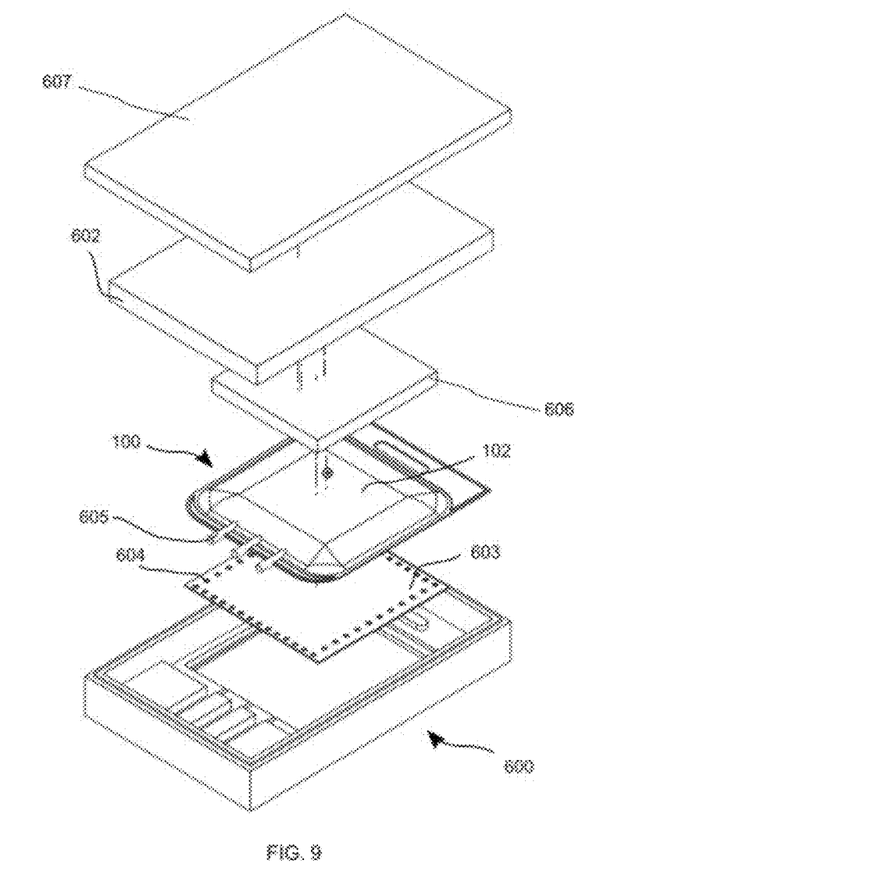
FIG. 9 is an exploded elevated view of the system.
Figure 10:
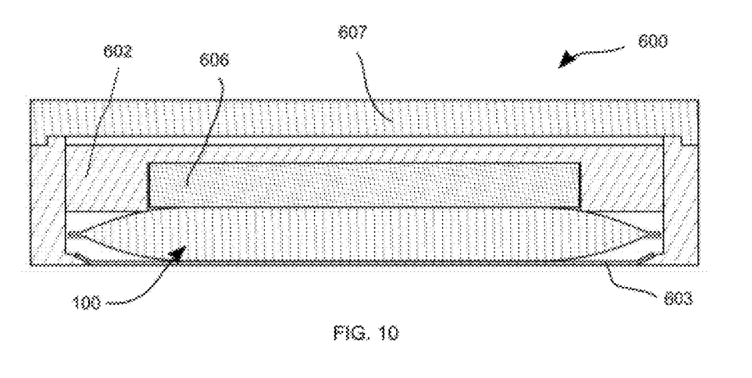
FIG. 10 is a cross-section view of the system.
Figure 11:
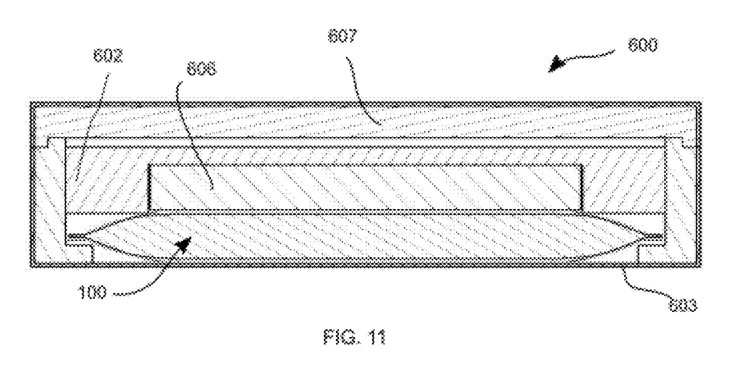
FIG. 11 is a cross-section view of the system.

In an embodiment, as illustrated in FIG. 9 as an exploded view and in FIG. 10 and FIG. 11 as a cross-section view, the present disclosure describes a case 600 to receive a bag 100 that can be used for freezing, transport, storage and/or thawing. In an embodiment, the case 600 may have a heat transfer plate 604 at the bottom to promote the heat transfer in the bottom surface 101 of the bag. The heat transfer plate 604 at the bottom surface of the case 600 could be made of a high heat conductive material, such as aluminium, to assure the heat transfer to the bottom of the bag inside the case.

Figure 12:
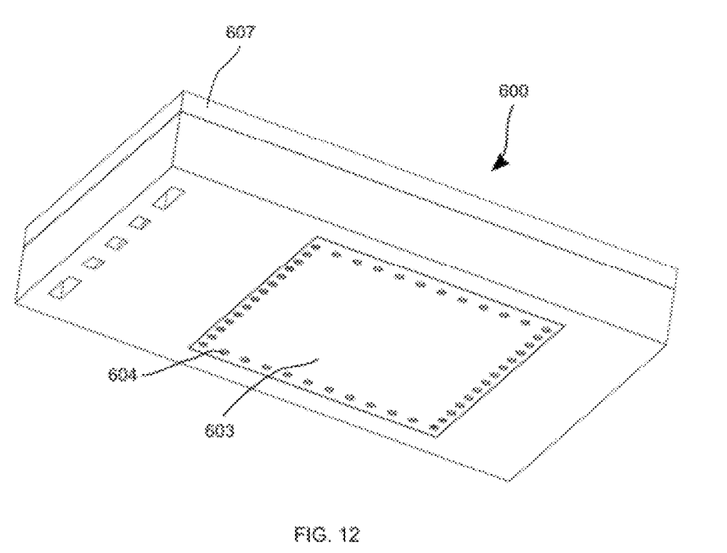
FIG. 12 is a bottom view of the system.

In an embodiment, as illustrated in FIGS. 9 and 12, the heat transfer plate 603 at the bottom may further comprise perforated holes 604 to achieve a high heat transfer coefficient at the edges of the bag thus ensuring nucleation and uniform bottom-up freezing. In addition, the perforated plate allows the air to flow through the tubes 605 of the bag, promoting its controlled freezing.

In an embodiment, as illustrated in FIG. 10, the heat transfer plate 603 at the bottom surface is configured to ensure a good thermal contact with the bottom and edged of the bag. The heat transfer plate can be shaped or folded depending on the shape of the bag 100.

In an embodiment, as illustrated in FIG. 11, the metal plate 603 is configured to cover the whole case to function as a heat transfer plate at the bottom of the bag 101 and also for physical protection of the whole case 600.

In an embodiment, the case 600 is made of polymers or materials that have low heat conductivity. For example, the case may be made of extruded polystyrene.

In an embodiment, as illustrated in FIG. 9, FIG. 10 and FIG. 11, an additional layer of a phase-change material 606 may be placed at the top surface of the bag 102 in order to further prevent ice growth at the top of the bag, while promoting bottom-up freezing.

Figure 13:
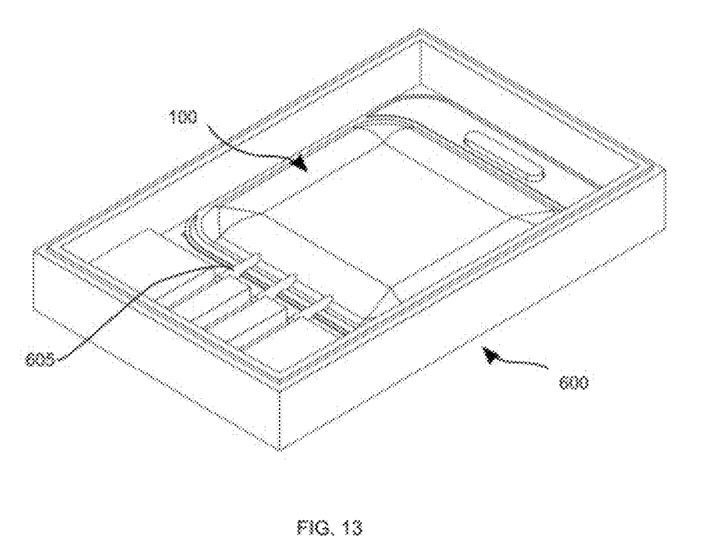
FIG. 13 is an elevated view of the system.

In an embodiment, as illustrated in FIG. 9 and FIG. 13, the bottom of the case 600 is configured to receive the bag 100 and the tubing assembly 605 ensuring that the tubes are fixed in place.

In an embodiment, the case 600 comprises a top lid 607 to close the case. The case can also be used as a carried to transport the bag.

In an embodiment, as illustrated in FIG. 14 as a cross-section view and FIG. 15 as an elevated view of the system, the system may be configured in a stacked configuration. The cases are configured to be stacked so that multiple cases may be used at the same time. The cases 600 in the stacked configuration are configured such that they comprise channels 402 for driving the air flow 200 from the bottom of the bag placed in a first case, to the bottom of the bag in a second case that is stacked immediately vertically on top of the first case. FIG. 14 illustrates how the differential air flow 200 circulates in the system configured in a stacked configuration. 402 represents the channel for air flow 200.

In an embodiment, the stacked configuration of the system comprises multiple layers, preferably at least 2 layers, more preferably at least 3 layers.

The term "bottom of the bag" whenever used in this document is intended to refer to the portion of the bag that is in contact with the higher air flow velocity, or the heat transfer plate, or the support on which the bag is placed on.

The term "comprising" whenever used in this document is intended to indicate the presence of stated features, integers, steps, components, but not to preclude the presence or addition of one or more other features, integers, steps, components or groups thereof.

It will be appreciated by those of ordinary skill in the art that unless otherwise indicated herein, the particular sequence of steps described is illustrative only and can be varied without departing from the disclosure. Thus, unless otherwise stated the steps described are so unordered meaning that, when possible, the steps can be performed in any convenient or desirable order.

The disclosure should not be seen in any way restricted to the embodiments described and a person with ordinary skill in the art will foresee many possibilities to modifications thereof.

The above described embodiments are combinable. The following claims further set out particular embodiments of the disclosure.

The invention claimed is:

1. A method for freezing an individual bag or a plurality of bags containing biological fluid, favoring bottom-up ice-growth, comprising the following steps: providing a controlled temperature chamber; placing an air flow system into the controlled temperature chamber; placing a bag or a case containing the bag on a support; compressing the bag or case against the support; driving air inside the controlled temperature chamber to obtain a differential air flow for freezing the bag, wherein the differential air flow is obtained by blowing air on the bottom of the bag or case such that a velocity of the air on the bottom of the bag or case is higher than a velocity of the air on the top of the bag or case, allowing bottom-up ice-growth; wherein a heat transfer coefficient on the top of the bag is less than 5 $W/(m^{2\circ} C.)$ and a heat transfer coefficient on the bottom of the bag is higher than 20 $W/(m^{2\circ} C.)$, and wherein the air flow has a velocity in a range from 1 m/s to 10 m/s.

2. The method of claim 1, wherein the heat transfer coefficient of the freezing biological fluid at a bottom of the bag is at least 10 times larger than at a top of the bag.

3. The method of claim 1, wherein the heat transfer coefficient at the top of the bag is less than 2 $W/(m^{2\circ} C.)$ and the heat transfer coefficient at the bottom of the bag is greater than 50 $W/(m^{2\circ} C.)$, wherein the velocity of the cold air below the bag or case is in a range from approximately 2 m/s to approximately 8 m/s.

4. The method of claim 1, wherein the air flow system comprises a fan and a flow conveyor, and the differential air flow is further obtained by blowing the cold air through the flow conveyor and at a bottom of the bag or case or at the support using the fan.

5. The method of claim 1, wherein the support is a heat transfer plate.

6. An air flow system for placing in a controlled temperature chamber having cold air at a temperature sufficient to freeze biological fluid in a bag, favoring bottom-up ice-growth, comprising: a support for holding the bag or a case containing the bag; and a rigid material with low heat conductivity to compress the held bag or case against the support, wherein the air flow system is configured to drive the cold air inside the controlled temperature chamber in order to obtain a differential air flow for freezing the biological fluid in the bag, wherein the differential air flow is obtained by blowing the cold air below the compressed bag or case such that velocity of the cold air below the bag or case is higher than velocity of the cold air above the bag or case, allowing bottom-up ice-growth of the biological fluid in the bag.

7. The air flow system according to claim 6, wherein a heat transfer coefficient at a top of the bag is less than 5 $W/(m^{2\circ} C.)$ and the heat transfer coefficient at a bottom of the bag is greater than 20 $W/(m^{2\circ} C.)$.

8. The air flow system according to claim 6, further comprising at least one fan, wherein and a controller for controlling a-velocity of the at least one fan is controllable.

9. The air flow system according to claim 8, further comprising a flow conveyor to drive the cold air from the at least one fan to a bottom surface of the compressed bag or case.

10. The air flow system according to claim 8, wherein the support presents a horizontal surface to the compressed bag or case, and the at least one fan drives the cold air in a direction parallel to the horizontal surface.

11. The air flow system according to claim 6, wherein the bag comprises a plurality of bags arranged in a horizontal plane configuration on the support, or the bag comprises a plurality of bags contained in a corresponding plurality of cases arranged in a horizontal place configuration on the support, or the bag comprises a plurality of bags contained in a corresponding plurality of cases arranged in a vertical stacked configuration on the support and comprising at least 2 layers, each layer including at least one of the plurality of cases.

12. The air flow system according to claim 11, wherein the plurality of cases are arranged in the vertical stacked configuration and further comprise air flow channels between layers to allow the cold air to flow such that in each layer, a bottom of each bag or case in the layer is exposed to a higher velocity of the cold air flow than a top of the bag or case.

13. The air flow system according to claim 6, wherein the support comprises fins.

14. The air flow system according to claim 13, wherein the support and the fins are made of high heat conductive material.

15. The air flow system according to claim 6, further comprising a case to receive a bag, wherein a bottom of the case has an opening or a thin film of a high heat conductive material.

16. The air flow system according to claim 6, further comprising a case to receive a bag, wherein the case is made of a low heat conductivity material.

17. The air flow system according to claim 6, further comprising a case to receive a bag, wherein a top of the case has a layer of a low heat conductive material.

18. The air flow system according to claim 6, further comprising an automated mechanical actuator to compress the held bag or case against the support.

* * * * *